United States Patent [19]
Michel et al.

[11] Patent Number: 5,965,760
[45] Date of Patent: Oct. 12, 1999

[54] PROCESS FOR REDUCING THE SULFANE CHAIN LENGTH OF BIS(SILYLORGANYL) POLYSULFANES

[75] Inventors: Rudolf Michel, Freigericht; Jorg Munzengerg, Hanau, both of Germany

[73] Assignee: Degussa Aktiengesellschaft, Frankfurt, Germany

[21] Appl. No.: 09/191,190

[22] Filed: Nov. 13, 1998

[30] Foreign Application Priority Data

Nov. 14, 1997 [DE] Germany ............... 197 50 503

[51] Int. Cl.$^6$ ....................................... C07F 7/08
[52] U.S. Cl. ................................................ 556/427
[58] Field of Search ................................. 556/427

[56] References Cited

U.S. PATENT DOCUMENTS 5,663,395  9/1997  Gobel et al. ...................... 556/427

*Primary Examiner*—Paul F. Shaver
*Attorney, Agent, or Firm*—Pillsbury Madison & Sutro LLP

[57] ABSTRACT

This invention relates to a process for reducing the sulfane chain length of bis(silylorganyl)polysulfanes, in which these compounds are reacted with an anhydrous sulfide and a haloalkylsilane compound.

25 Claims, No Drawings

PROCESS FOR REDUCING THE SULFANE CHAIN LENGTH OF BIS(SILYLORGANYL) POLYSULFANES

This application is based on application No. 19750503.1 filed in Germany on Nov. 14, 1997, the content of which is incorporated hereinto by reference.

BACKGROUND OF THE INVENTION

1. Field of the Invention

This invention relates to a process for reducing the sulfane chain length of bis(silylorganyl)polysulfanes by reacting these compounds with a sulfide and a haloalkyl-silane.

2. Prior Art

Polysulfanes of this type have long been known (DE-PS 2255577) and are widely used as reinforcing additives in rubber vulcanisates containing silica, in particular in the tyre sector. Bis(triethoxysilylpropyl)tetrasulfane (Si 69, Degussa AG) has in particular become established in such applications (c.f. Wolff, 129$^{th}$ Meeting of the Rubber Division, American Chemical Society, Apr. 8–11, 1986, NY).

The processing advantages of corresponding disulfanes have recently been described in various publications. These compounds should be incorporated into the rubber compositions as the purest possible compounds according to EP-A-0732 362 (U.S. Pat. No. 5,580,919) or alternatively in the form of mixtures (DE-OS 197 0246.1).

However, according to the prior art, disulfanes are produced under unpleasant conditions as mercaptosilanes must be oxidised with manganese dioxide (EP-A 0718 302).

SUMMARY OF THE INVENTION

The object of the invention is to provide a process which yields the desired product without these accompanying phenomena.

The present invention provides a process for reducing the sulfane chain length of bis(silylorganyl)polysulfanes, characterised in that an organosilicon compound of the general formula $$Z\text{-}Alk\text{-}S_x\text{-}Alk\text{-}Z \quad (I)$$

in which Z denotes groupings

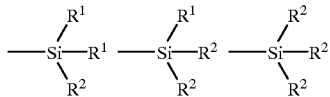

in which $R^1$ represents a linear or branched alkyl group having 1 to 5 C atoms, a cycloalkyl residue having 5 to 8 C-atoms, the benzyl residue or the phenyl residue optionally substituted by methyl, ethyl or chlorine, $R^2$ denotes an alkoxy group having a linear or branched carbon chain having 1 to 5 C atoms or a cycloalkoxy group having 5 to 8 C atoms, the phenoxy group or the benzyl group, wherein $R^1$ and $R^2$ may each have identical or different meanings, Alk denotes a divalent saturated or monounsaturated linear or branched hydrocarbon residue having 1–10 C atoms, in particular 1 to 4 C atoms or the group

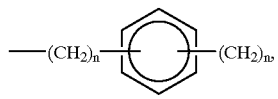

x denotes an integer from 3 to 8, in particular from 4 to 6 and n denotes an integer from 1 to 4 is reacted with an anhydrous sulfide of the general formula $$Me_2S \quad (II),$$

in which Me represents an alkali metal, in particular sodium or an equivalent of an alkaline earth metal atom or of zinc or ammonium, and an organosilicon compound of the general formula $$Z\text{-}Alk\text{-}Y \quad (III)$$

in which Z and Alk have the above-stated meanings and Y means Cl, Br, wherein the molar ratio of the polysulfane and of the $Me_2S$ is selected in accordance with the desired sulfur content of the polysulfane to be partially desulfurised.

In one particular embodiment, x denotes a statistical mean, as the corresponding pure polysulfane may often be produced only with difficulty.

By appropriate adjustment of the molar ratios, it is possible to produce mixtures of different polysulfanes, in which for example the disulfanes predominate (DE-OS 19702046) or also very pure disulfanes, as are used according to U.S. Pat. No. 5,580,919.

The reaction ratios are generally selected such that the compound of the formula (II) is added to the reaction mixture in a quantity (mol) which is at least sufficient completely to react with the $S_y$ groups newly formed by the sulfur fraction from the desulfurisation and the added $Na_2S$ to yield compounds of the formula (I), wherein $y<x\geq 1$ corresponds to the length of the sulfane chain formed by the desulfurisation.

The reaction preferably proceeds in an organic, preferably polar solvent which is inert under the test conditions. Such solvents include in particular aliphatic alcohols having 1 to 6 C atoms, ethers having $C_2$–$C_{12}$ C atoms, amides, such as for example dimethylformamide, sulfoxides, such as for example dimethyl sulfoxide.

The reaction generally proceeds at temperatures of 50° C. up to the reflux temperature of the solvent used, optionally under the pressure which is established at this temperature. The product obtained in particular has a chain length $S_y$ where $y=2$.

A tetrasulfane is preferably used in order to shorten the sulfane chain length. This applies in particular to the readily available bis(triethoxysilylpropyl)tetrasulfane. The corresponding trisulfane is produced from a tetrasulfane by adjusting the molar ratios of the reactants tetrasulfane, $Me_2S$ and compounds of the formula (II) to 1:0.4 to 0.6:0.9 to 1.1.

Ratios of 1:1.8 to 2.2:2.5 to 3.5 are required for the production of the disulfane from the tetrasulfane.

Preferably used compounds of the formula (II) are those giving rise to a symmetrical polysulfane molecule.

DETAILED DESCRIPTION OF PREFERRED EMBODIMENTS OF THE INVENTION

Examples

Example 1

Reduction of average chain length from 4 to 2.

67.4 g (0.13 mol) of bis(3-triethoxysilylpropyl)-tetrasulfane and 15.5 g (0.24 mol) of sodium sulfide in 120 ml of ethanol were introduced under $N_2$ protective gas into a 500 ml, three-necked flask with a reflux condenser and magnetic stirrer. 108.7 g (0.45 mol) of 3-chloropropyltriethoxysilane were added thereto at room temperature and the reaction mixture maintained at reflux temperature for 2.5 hours. After cooling to room temperature, the precipitate was filtered out and the filtration residue washed three times with 30 ml of ethanol. The collected filtrates were evaporated in a rotary evaporator at 100° C. down to a final vacuum of 40 mbar. 153.1 g of a yellow liquid were obtained which, according to $^1$H-NMR spectroscopic analysis, comprises a polysulfane mixture having an average polysulfane chain length of 2.

Yield: 90%.

Example 2

Reduction of average chain length from 4 to 3

100 g (0.19 mol) of bis(3-triethoxysilylpropyl)-tetrasulfane and 7.8 g (0.1 mol) of sodium sulfide in 100 ml of ethanol were introduced under $N_2$ protective gas into a 500 ml, three-necked flask with a reflux condenser (droplet condenser) and magnetic stirrer and refluxed for 1 hour. 48.2 g (0.2 mol) of 3-chloropropyltriethoxysilane were added thereto and the reaction mixture maintained at reflux temperature for a further 2.5 hours. After cooling to room temperature, the precipitate was filtered out and the filtration residue washed three times with 30 ml of ethanol. The collected filtrates were evaporated in a rotary evaporator at 110° C. down to a final vacuum of 40 mbar. 144.9 g of a red-brown liquid were obtained which, according to $^1$H-NMR spectroscopic analysis, comprises a polysulfane mixture having an average polysulfane chain length of 3.

Yield: 98%.

What is claimed is:

1. A process for reducing the sulfane chain length of bis(silylorganyl)polysulfanes, wherein an organosilicon compound of the general formula $$Z\text{-}Alk\text{-}S_x\text{-}Alk\text{-}Z \qquad (I)$$

in which Z denotes groupings

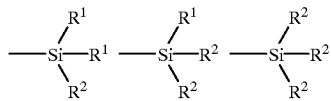

in which $R^1$ represents a linear or branched alkyl group having 1 to 5 C atoms, a cycloalkyl residue having 5 to 8 C atoms, the benzyl residue or the phenyl residue optionally substituted by methyl, ethyl or chlorine, $R^2$ denotes an alkoxy group having a linear or branched carbon chain having 1 to 5 C atoms or a cycloalkoxy group having 5 to 8 C atoms, the phenoxy group or the benzyl group, wherein $R^1$ and $R^2$ may each have identical or different meanings, Alk denotes a divalent saturated or monounsaturated linear or branched hydrocarbon residue having 1–10 C atoms or the group

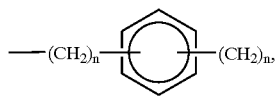

x denotes an integer from 3 to 8, in particular from 4 to 6 and n denotes an integer from 1 to 4 is reacted with an anhydrous sulfide of the general formula $$Me_2S \qquad (II)$$

in which Me represents an alkali metal, in particular sodium or an equivalent of an alkaline earth metal atom or of zinc or ammonium, and an organosilicon compound of the general formula $$Z\text{-}Alk\text{-}Y \qquad (III)$$

in which Z and Alk have the above-stated meanings and Y means Cl, Br, wherein the molar ratio of the polysulfane and of the $Me_2S$ is selected in accordance with the desired sulfur content of the polysulfane to be partially desulfurised and of the desired product, and the desulfurised polysulfane is obtained pure or in the form of a mixture with other polysulfanes.

2. A process according to claim 1, wherein the compound of the formula (II) is added to the reaction solution in a quantity (mol) which is at least sufficient completely to react with the $S_y$ groups newly formed by the sulfur fraction from the desulfurisation and the added $Na_2S$ to yield compounds of the formula (I), wherein $y < x \geq 1$ corresponds to the length of the sulfane chain formed by the desulfurisation.

3. A process according to claims 1 or 2, wherein an organic, inert and preferably polar solvent is used.

4. A process according to claim 3, wherein the reaction is performed at a temperature of 50° C. up to the reflux temperature of the solvent.

5. A process according to claims 1 or 2, wherein x in the formula (I) and correspondingly y correspond to a statistical mean.

6. A process according to claim 3, wherein x in the formula (I) and correspondingly y correspond to a statistical mean.

7. A process according to claim 4, wherein x in the formula (I) and correspondingly y correspond to a statistical mean.

8. A process according to claims 1 or 2, wherein a bis(silylorganyl)tetrasulfane is desulfurised.

9. A process according to claim 3, wherein a bis (silyorganyl) tetrasulfane is disulfurised.

10. A process according to claim 4, wherein a bis (silyorganyl) tetrasulfane is desulfurised.

11. A process according to claim 5, wherein a bis (silyorganyl) tetrasulfane is desulfurised.

12. A process according to claim 6, wherein a bis (silyorganyl) tetrasulfane is desulfurised.

13. A process according to claim 7, wherein a bis (silyorganyl) tetrasulfane is desulfurised.

14. A process according to claim 8, wherein a trisulfane is produced from the tetrasulfane by adjusting the molar ratios of the reactants tetrasulfane, $Me_2S$ and compounds of the formula (III) to 1:0.4 to 0.6:0.9 to 1.1.

15. A process according to claim 9, wherein a trisulfane is produced from the tetrasulfane by adjusting the molar ratios of the reactants tetrasulfane, $Me_2S$ and compounds of the formula (III) to 1:0.4 to 0.6:0.9 to 1.1.

16. A process according to claim 10, wherein a trisulfane is produced from the tetrasulfane by adjusting the molar ratios of the reactants tetrasulfane, $Me_2S$ and compounds of the formula (III) to 1:0.4 to 0.6:0.9 to 1.1.

17. A process according to claim 11, wherein a trisulfane is produced from the tetrasulfane by adjusting the molar ratios of the reactants tetrasulfane, $Me_2S$ and compounds of the formula (III) to 1:0.4 to 0.6:0.9 to 1.1.

18. A process according to claim 12, wherein a trisulfane is produced from the tetrasulfane by adjusting the molar ratios of the reactants tetrasulfane, $Me_2S$ and compounds of the formula (III) to 1:0.4 to 0.6:0.9 to 1.1.

19. A process according to claim 13, wherein a trisulfane is produced from the tetrasulfane by adjusting the molar ratios of the reactants tetrasulfane, $Me_2S$ and compounds of the formula (III) to 1:0.4 to 0.6:0.9 to 1.1.

20. A process according to claim 8, wherein a disulfane is produced from the tetrasulfane by adjusting the molar ratios of the reactants tetrasulfane, $Me_2S$ and compounds of the formula (III) to 1:1.8 to 2.2:2.5 to 3.5.

21. A process according to claim 9, wherein a disulfane is produced from the tetrasulfane by adjusting the molar ratios of the reactants tetrasulfane, $Me_2S$ and compounds of the formula (III) to 1:1.8 to 2.2:2.5 to 3.5.

22. A process according to claim 10, wherein a disulfane is produced from the tetrasulfane by adjusting the molar ratios of the reactants tetrasulfane, $Me_2S$ and compounds of the formula (III) to 1:1.8 to 2.2:2.5 to 3.5.

23. A process according to claim 11, wherein a disulfane is produced from the tetrasulfane by adjusting the molar ratios of the reactants tetrasulfane, $Me_2S$ and compounds of the formula (III) to 1:1.8 to 2.2:2.5 to 3.5.

24. A process according to claim 12, wherein a disulfane is produced from the tetrasulfane by adjusting the molar ratios of the reactants tetrasulfane, $Me_2S$ and compounds of the formula (III) to 1:1.8 to 2.2:2.5 to 3.5.

25. A process according to claim 13, wherein a disulfane is produced from the tetrasulfane by adjusting the molar ratios of the reactants tetrasulfane, $Me_2S$ and compounds of the formula (III) to 1:1.8 to 2.2:2.5 to 3.5.

* * * * *